(12) United States Patent  
Ramrattan

(10) Patent No.: US 9,121,804 B2  
(45) Date of Patent: Sep. 1, 2015

(54) THERMAL EROSION TESTER

(71) Applicant: Western Michigan University Research Foundation, Kalamazoo, MI (US)

(72) Inventor: Sam N. Ramrattan, Kalamazoo, MI (US)

(73) Assignee: Western Michigan University Research Foundation, Kalamazoo, MI (US)

( * ) Notice: Subject to any disclaimer, the term of this patent is extended or adjusted under 35 U.S.C. 154(b) by 369 days.

(21) Appl. No.: 13/837,601

(22) Filed: Mar. 15, 2013

(65) Prior Publication Data

US 2013/0243027 A1   Sep. 19, 2013

Related U.S. Application Data

(60) Provisional application No. 61/611,037, filed on Mar. 15, 2012.

(51) Int. Cl.
| | |
|---|---|
| *G01N 17/00* | (2006.01) |
| *G01K 7/00* | (2006.01) |
| *G01N 25/00* | (2006.01) |
| *G01N 3/56* | (2006.01) |

(52) U.S. Cl.
CPC .................. *G01N 25/00* (2013.01); *G01N 3/56* (2013.01); *G01N 3/565* (2013.01)

(58) Field of Classification Search
CPC .......... G01N 17/00; G01N 25/00; G01K 7/00
See application file for complete search history.

(56) References Cited

U.S. PATENT DOCUMENTS

| 3,165,924 | A | * | 1/1965 | Wolff | 73/112.01 |
|---|---|---|---|---|---|
| 3,391,102 | A | * | 7/1968 | Major | 523/138 |
| 3,404,557 | A | * | 10/1968 | Hecht et al. | 73/7 |
| 4,523,475 | A | * | 6/1985 | Bills et al. | 73/781 |
| 4,561,784 | A | * | 12/1985 | Benz et al. | 374/8 |
| 4,759,215 | A | * | 7/1988 | Atchley et al. | 73/167 |
| 5,113,650 | A | * | 5/1992 | Junior et al. | 60/253 |
| 5,419,116 | A | * | 5/1995 | Rast et al. | 60/204 |
| 5,419,119 | A | * | 5/1995 | Obney | 60/253 |
| 6,054,521 | A | * | 4/2000 | Nelson et al. | 524/405 |
| 7,628,534 | B2 | * | 12/2009 | Deoclezian et al. | 374/7 |

FOREIGN PATENT DOCUMENTS

| CN | 102042902 A | 4/2011 |
|---|---|---|
| SU | 970201 A1 | 10/1982 |

OTHER PUBLICATIONS

International Search Report and Written Opinion, Sep. 5, 2013, from International Application No. PCT/US2013/041168, 6 pages.

* cited by examiner

*Primary Examiner* — Lisa Caputo
*Assistant Examiner* — Jamel Williams
(74) *Attorney, Agent, or Firm* — Price Heneveld LLP

(57) ABSTRACT

A thermal erosion tester, comprising a rotating heated element, which is adapted to contact a sand specimen placed in the thermal erosion tester, a heating element to heat the rotating heated element, and a motor to drive rotation of the rotating heated element, wherein the rotating heated element is adapted to contact the sand specimen while the rotating heated element is rotating, causing erosion of the sand specimen, and a method of testing thermal erosion, and a method of testing erosion of a sand specimen when it is in contact with a heated element.

20 Claims, 5 Drawing Sheets

THERMAL EROSION TESTER

CROSS REFERENCE TO RELATED APPLICATIONS

This application claims priority under 35 U.S.C. §119(e) to U.S. Provisional Patent Application No. 61/611,037, filed Mar. 15, 2012, entitled "THERMAL EROSION TESTER", which is herein incorporated by reference in its entirety.

BACKGROUND OF THE INVENTION

Bonded sand cores and molds, comprising mixtures of sand, and clay or chemical binders, and optionally refractory coatings, are an important part of metal casting technology. The behavior of the bonded sand cores and molds or green sand cores and molds, when placed in contact with molten metal, is important to control the quality of metal castings formed using these sand cores and molds. Friability of the sand mixture is one factor that affects the quality of castings using a bonded sand core or mold.

Friability is the ability of a solid substance to be reduced to smaller pieces, and the friability of a sand mixture is considered a measure of the sand's abrasion resistance. A friable sand mixture is a sand mixture that is not able to withstand the erosive flow of molten metal during casting. Friable sand mixtures lose sand grains to the flowing molten stream, and the loose sand causes additional erosion and inclusion defects. As the friability of the sand mixture used in a mold increases, the ability to draw deep pockets decreases, and sand from the top half of the mold falls into the bottom half of the mold, and leads to a defect in the casting. Mold sand mixtures can become very friable if there is too high an influx of core sand or new sand and bond during the mixing process. New bond requires several passes through a mixer before its properties are developed.

Friability is inversely related to compactibility. The lower the compactibility, the higher the friability. Some mold sands, depending upon their composition and moisture and/or clay content are extremely moisture sensitive in relation to their compactibility.

In the current standard AFS friability test, two standard AFS sand specimens (specimens which are cylindrically shaped, 2 inches in diameter by 2 inches tall) are placed side-by-side in a 7 inch diameter cylindrical screen, and then the screen is rotated for one minute causing the specimens to rotate and rub against each other. The test is normally performed immediately after specimen preparation, but can be tested after various air drying intervals. As the specimens rotate, the sand abraded from the surface is collected in a pan. Weight loss is normally expressed as the weight loss of the sand specimens divided by the original starting weight (of both specimens), and multiplied by 100 to produce the "percent friability." Work of the AFS Green Sand Test Committee suggests that a friability level of under 10% is generally satisfactory for use in molds and cores. If friability of the sand mixture is greater than 10%, a mold incorporating the sand mixture will be subject to erosion and inclusion-type defects when used with molten metal.

The presently used AFS friability test is run at room temperature, and involves the rubbing together of two room temperature sand specimens. The current friability test also does not take in to account the pressure that is created when pouring molten metal from height. The presently used friability test also does not have any mechanism or variation to represent the ratio of metal to sand. Therefore, the current test of rubbing two specimens together does not accurately depict what is happening in a real-world casting situation.

SUMMARY OF THE INVENTION

One aspect of the present invention includes an apparatus for performing a thermal erosion test on a sand specimen including a specimen holder which supports the sand specimen. A rotating heated element is disposed below the specimen holder and is operably rotated by a motor. The rotating heated element is adapted to extend through an opening in the specimen holder to contact the specimen while the rotating heated element is being operably rotated by the motor. A funnel is disposed below the specimen holder, wherein the funnel is adapted to catch loose sand abraded from the specimen by the contact of the rotating heated element with the specimen. A weighing element is adapted to detect the weight of the loose sand.

Another aspect of the invention includes an apparatus for performing a thermal erosion test on a sand specimen, including a heated element. A motor is operably engaged with the heated element and rotates the heated element when the heated element is brought into contact with the sand specimen. A member is provided to collect loose sand abraded from the sand specimen by the rotation of the heated element.

Another aspect of the invention includes a method of performing a friability test on a sand specimen. The method includes the steps of supporting a sand specimen above a heated element. The sand specimen has a tapered hole therein. The heated element and the sand specimen are brought into contact, with the heated element adjacent the tapered hole of the sand specimen. The heated element is rotated a pre-determined amount, any loose sand abraded from the sand specimen is collected, and the loose sand is weighed.

DETAILED DESCRIPTION

Figure 1:
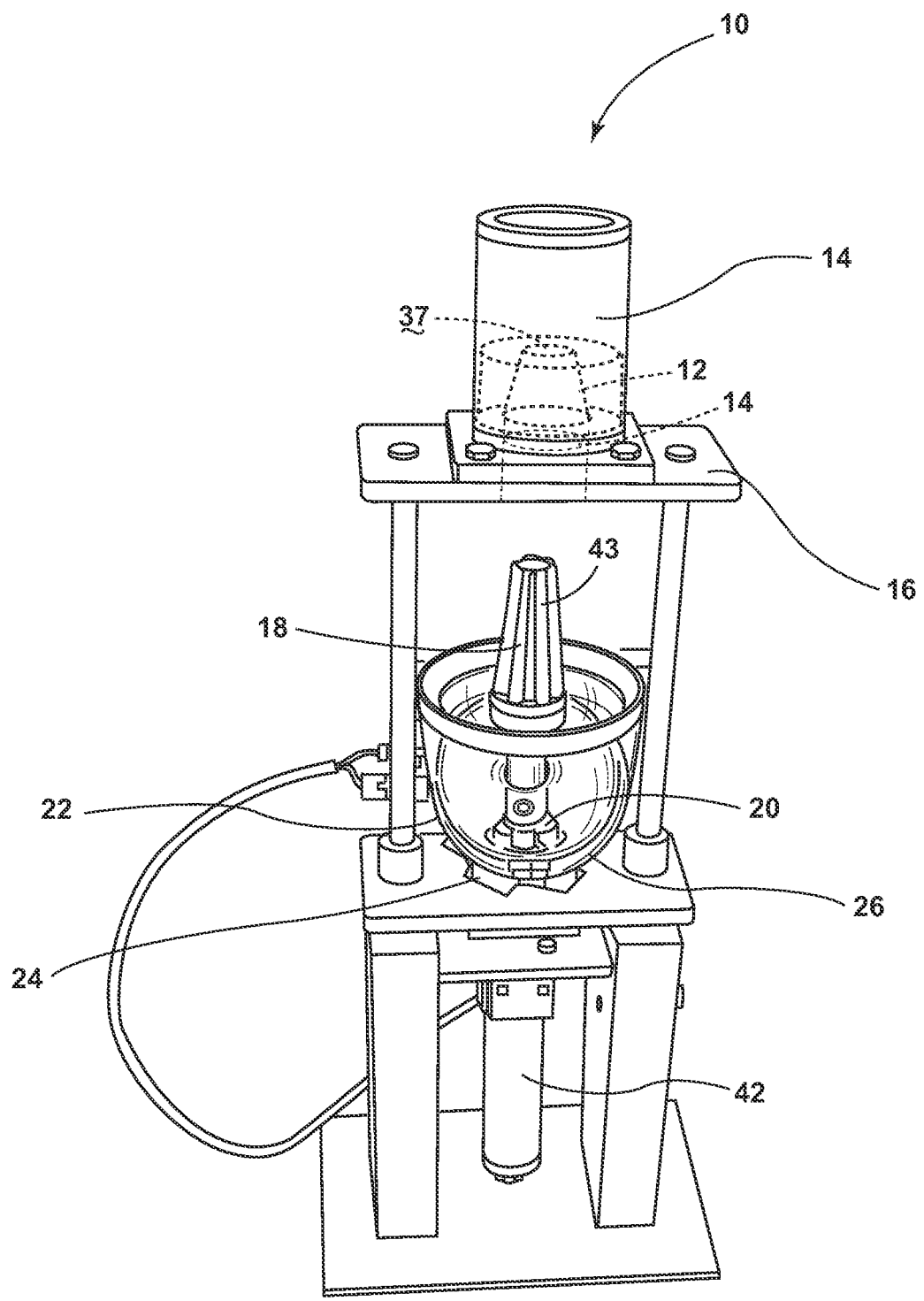
FIG. 1 is a top perspective view of an embodiment of a thermal erosion tester.
Figure 1A:
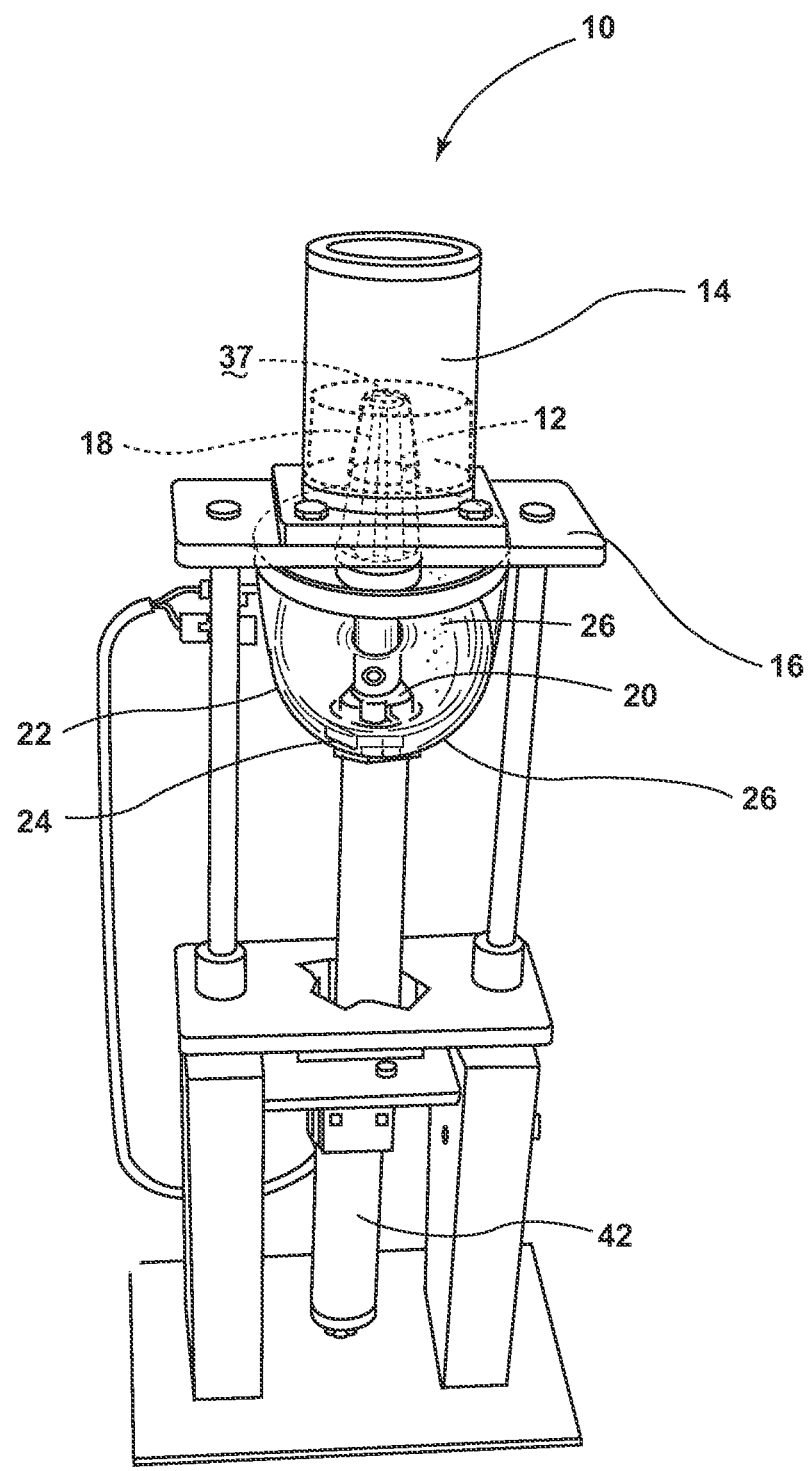
FIG. 1A is a top perspective view of the thermal erosion tester shown in FIG. 1, in position to perform a thermal erosion test.

A preferred embodiment of a thermal erosion tester ("TET") 10 for testing the friability of a sand specimen 12, as shown in FIGS. 1-1A, comprises a cylindrical tube 14 to hold a sand specimen 12, a tube-specimen holder 16, a rotating heating element 18 mounted with a variable speed motor 20 to control its rotation, a funnel 22 to catch loose sand 26 which is abraded from sand specimen 12, and a weighing element 24 to weigh the sand 26 that is abraded from sand specimen 12 during the test.

Figure 2:
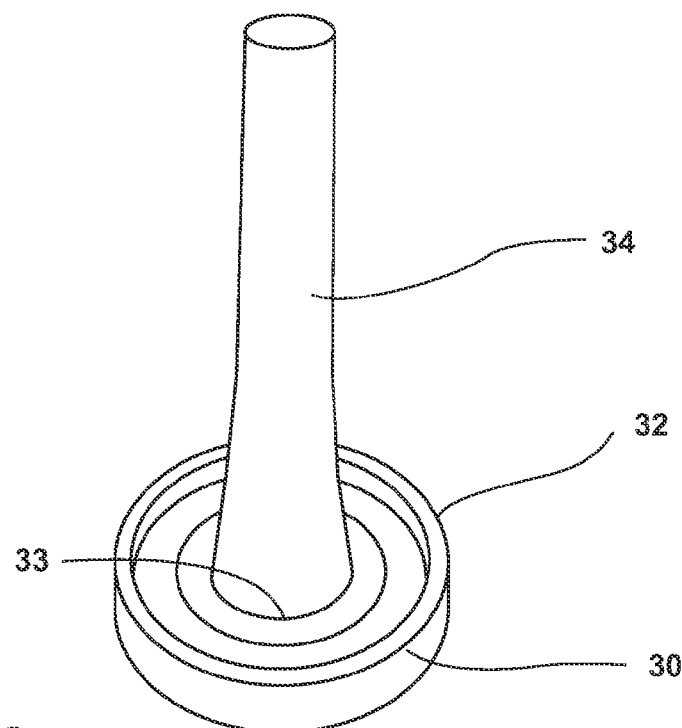
FIG. 2 is a top perspective view of a sand specimen producing base, with a guide installed thereon.
Figure 3:
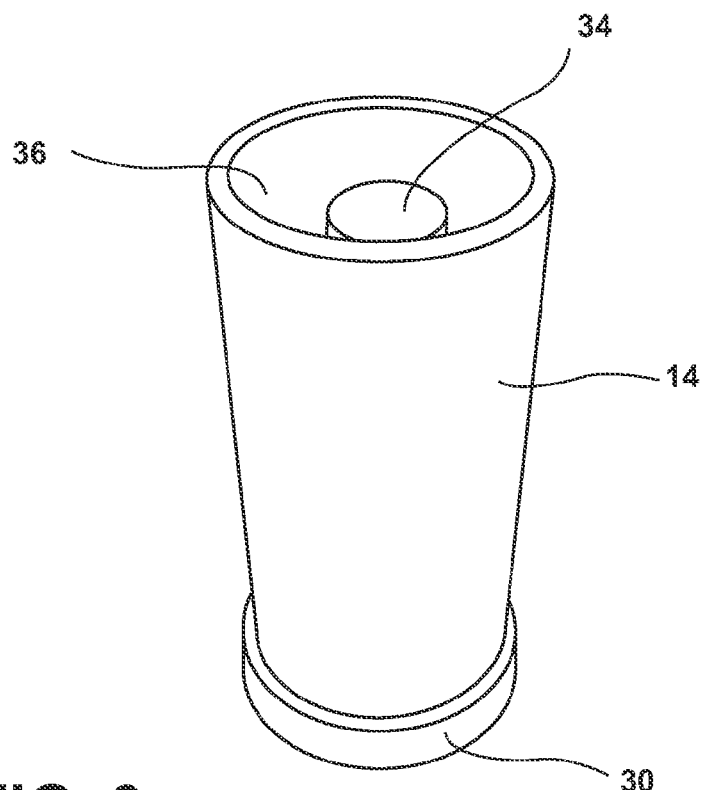
FIG. 3 is a top perspective view of the sand specimen producing base, with a guide and cylindrical tube installed thereon.

As best shown in FIG. 1, sand specimen 12 preferably comprises sand in a hollowed cylindrical shape. As used herein, "sand" includes without limitation, sand, a sand and binder mixture, or a sand and binder mixture with a refractory coating thereon. Accordingly, the "sand specimen" includes a specimen formed from any of the foregoing types of sand. The sand specimen 12 is made using a generally disc-shaped base 30 with a raised edge 32 extending upwards around the circumferential edge thereof. As shown in the embodiment depicted in FIG. 2, a cylindrical guide 34, having a diameter smaller than base 30 fits over the center portion of base 30, and extends upwardly therefrom. The end portion 33 of cylindrical guide 34 located adjacent base 30 when assembled with base 30 is tapered. The tapering preferably extends for about 2 inches of the length of cylindrical guide 34. As shown in the embodiment depicted in FIG. 3, a hollow, cylindrical tube 14, preferably an AFS standard 2" inner diameter tube, is then placed over base 30, and is held in place by raised edge 32, leaving an opening 36 between guide 34 and hollow cylindrical tube 14. Sufficient sand to create a specimen, which is 2 inches high and 2 inches in diameter, with a tapered hole 37 in the center is then weighed and poured into opening 36.

Figure 4:
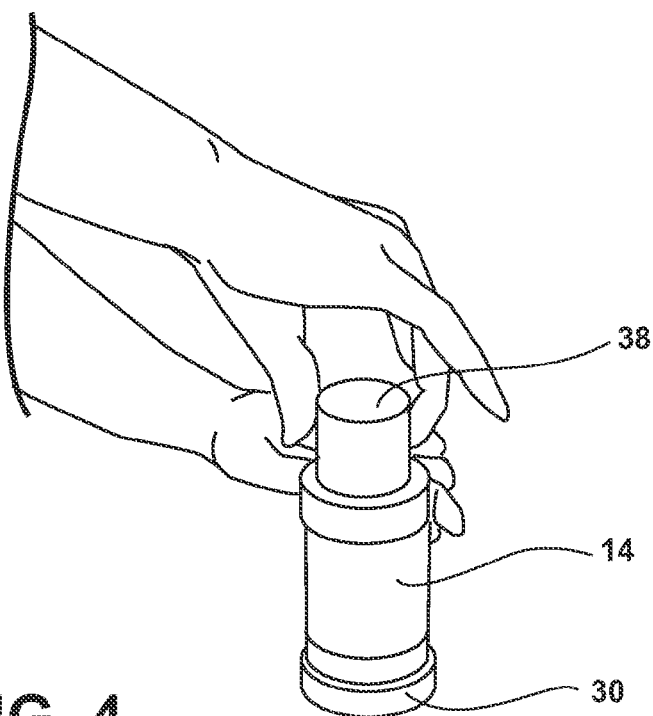
FIG. 4 is a top perspective view of the sand specimen producing base, with a guide and cylindrical tube installed thereon, and a pusher being used to compact the sand.
Figure 5:
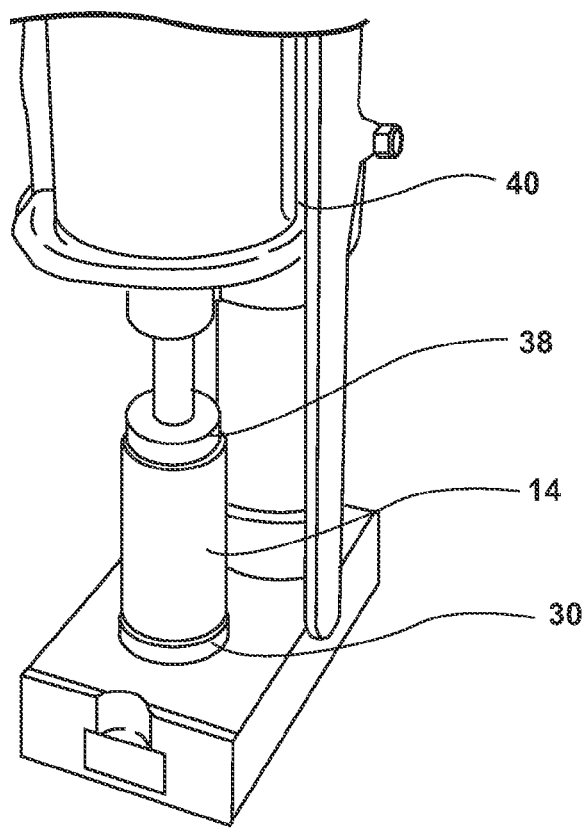
FIG. 5 is a top perspective view of the sand squeezer compacting the sand in the sand specimen producing base.

As shown in the embodiment depicted in FIG. 4, a pusher 38 is placed around guide 34, and pushed down by hand to pack sand into opening 36 and to prepare the sample for use of an automated sand squeezer 40. As shown in the embodiment depicted in FIG. 5, the automated sand squeezer 40 is activated until about 140 psi of pressure is applied to sand specimen 12, and the pressure is maintained for about 3 seconds. Following compaction of sand specimen 12, base 30, guide 34, and pusher 38 are removed from sand specimen 12, leaving sand specimen 12 having a tapered hole 37 through the center thereof in cylindrical tube 14.

As shown in the embodiment of the TET 10 depicted in FIGS. 1-1A, in operation, sand specimen 12 and cylindrical tube 14 are placed on the tube-specimen holder 16 of thermal erosion tester 10. Tube-specimen holder 16 has an opening 41 which allows passage of rotating heated element 18 up into the tapered hole 37 of sand specimen 12, as shown in FIGS. 1 and 1A. Rotating heated element 18 is preferably shaped congruently to the tapered hole 37 in sand specimen 12, such that it contacts sand specimen 12 along the entire length of the tapered hole 37 through the center thereof. For example, the shape of the rotating heated element 18 may be generally conical or frustroconical. Rotating heated element 18 preferably has a textured surface 43 to contact the sand specimen 12 to abrade the sand specimen 12. One example of such a textured surface 43 is a longitudinal ribbed pattern. Rotating heated element 18 is heated to a predetermined temperature, to model the temperature of molten metal that would be poured into a sand mold, when used for casting. Tube-specimen holder 16 may be lowered over rotating heated element 18 so that sand specimen 12 is brought into contact with rotating heated element 18, with rotating heated element 18 within the hollowed portion of sand specimen 12. Alternatively, rotating heated element 18 could be raised to contact sand specimen 12. Rotating heated element 18 may be raised using, for example, a hydraulic element 42. Rotating heated element 18 and sand specimen 12 are preferably brought into contact slowly, to avoid loss of sand specimen 12 as a result of contact between sand specimen 12 and rotating heated element 18 or as a result of the fast motion of sand specimen 12.

Sand specimen 12 sets on rotating heated element 18, and is held there by its own weight, or sand specimen 12 can be secured in place against rotating heated element 18 so that a pre-determined pressure can be applied to the sand specimen 12 by rotating heated element 18. Rotating heated element 18 can be rotated at varying speeds by motor 20. Rotating heated element 18 is then rotated from about ¼ revolution to about 1 revolution, during which rotation the rotating heated element 18 rubs against sand specimen 12, loosening and eroding some of the sand. Preferably, enough rotation is provided to produce measurable and reproducible results. Additionally, a speed for rotation is preferably chosen to increase reproducibility of sand loss with the same type of sand specimen 12.

Funnel 22 is placed below rotating heated element 18, so that as abraded sand 26 falls from sand specimen 12, it is caught in funnel 22. Funnel 22 is preferably a glass or plastic material. Weighing element 24 measures the mass of the sand collected in funnel 22. The weight of abraded sand 26, as well as its appearance can be monitored throughout the duration of the thermal erosion test.

During and after the test procedure, the coloration of the sand can be observed by the test operator. Elevated temperatures affect and damage the clay content or chemical binder in the sand. In a green sand specimen 12 that is abraded at room temperature, the sand which is abraded has a charcoal black color, which is the same color as the sand used in sand specimen 12 when it comes out of a mixer. When sand specimen 12 is tested at 300° C., the abraded sand is a gray color, and when sand specimen 12 is tested at 700° C., the abraded sand is a light gray color.

Figure 6:
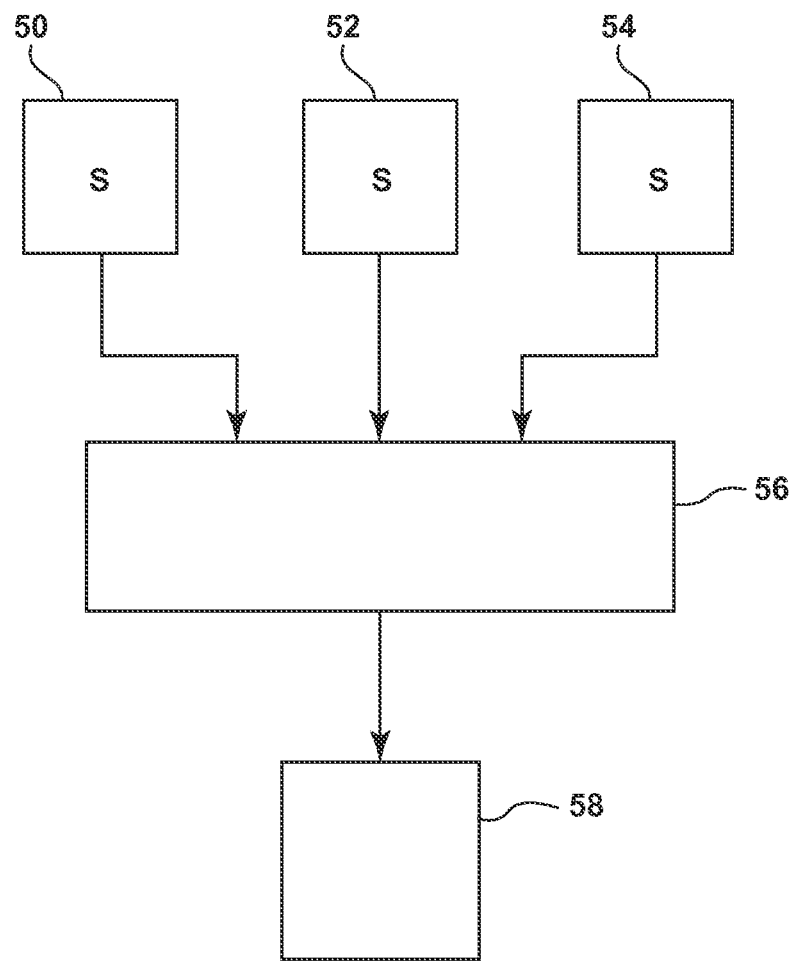
FIG. 6 is a schematic diagram illustrating the collection of data by the thermal erosion tester shown in FIG. 1.

As shown in FIG. 6, TET 10 measures bulk surface abrasion of sand specimen 12 at an elevated temperature. The TET 10 includes a sensor 50 to measure the elapsed time of the test, a sensor 52 to measure the temperature of the rotating heating element 18, and a sensor 54 to measure the weight of sand abraded from the sand specimen 12, all preferably in real time. Data collected by the sensors 50, 52, 54 is transmitted to a data acquisition system 56. The data acquisition system 56 records data collected by these sensors 50, 52, 54, optionally continuously through the duration of the test. Preferably, as data is collected by the data acquisition system 56, a graphical representation 58 such as a curve is also generated by the data acquisition system 56 showing change in mass of specimen 12 as a function of time.

The thermal erosion tester 10 described herein more closely replicates the response of a sand mold when it is used for casting molten metal. Thermal erosion tester 10 allows the operator to evaluate the reaction of sand specimen 12 when heat is applied thereto during the abrasion. As the types of sand used for a mold generally contain clay and/or other binders, heat may significantly change the friability of the sand. As clays and other binders are heated at the mold-metal interface of a mold, they denature and break down. Therefore, measuring the friability at the anticipated temperature of the mold-metal interface provides a more accurate determination of the mold's real-world performance. The test described herein also takes into account the pressure that is created when pouring molten metal from a height into a mold, also providing a more accurate representation of the actual circumstances encountered when molten metal is poured into a sand mold. The results of testing various sand and binder systems can be compared to determine relative erosion-resistance of the samples.

One aspect of the present invention includes an apparatus for performing a thermal erosion test on a sand specimen including a specimen holder which supports the sand specimen. A rotating heated element is disposed below the specimen holder and is operably rotated by a motor. The rotating heated element is adapted to extend through an opening in the specimen holder to contact the specimen while the rotating heated element is being operably rotated by the motor. A funnel is disposed below the specimen holder, wherein the funnel is adapted to catch loose sand abraded from the specimen by the contact of the rotating heated element with the specimen. A weighing element is adapted to detect the weight of the loose sand.

Another aspect of the invention includes an apparatus for performing a thermal erosion test on a sand specimen, including a heated element. A motor is operably engaged with the heated element and rotates the heated element when the heated element is brought into contact with the sand specimen. A member is provided to collect loose sand abraded from the sand specimen by the rotation of the heated element.

Another aspect of the invention includes a method of performing a friability test on a sand specimen. The method includes the steps of supporting a sand specimen above a heated element. The sand specimen has a tapered hole therein. The heated element and the sand specimen are brought into contact, with the heated element adjacent the tapered hole of the sand specimen. The heated element is rotated a pre-determined amount, any loose sand abraded from the sand specimen is collected, and the loose sand is weighed.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

The invention claimed is:

1. An apparatus for performing a thermal erosion test on a sand specimen, the apparatus comprising:
    a specimen holder which supports the sand specimen;
    a rotating heated element disposed below the specimen holder and operably rotated by a motor, wherein the rotating heated element is adapted to extend through an opening in the specimen holder to contact the specimen while the rotating heated element is being operably rotated by the motor;
    a funnel disposed below the specimen holder, wherein the funnel is adapted to catch loose sand abraded from the specimen by the contact of the rotating heated element with the specimen; and
    a weighing element adapted to detect the weight of the loose sand.

2. The apparatus of claim 1, wherein the motor which operably rotates the rotating heated element is a variable speed motor.

3. The apparatus of claim 1, wherein the heated element further comprises a contact surface which comes into contact with the specimen, and wherein the contact surface is textured.

4. The apparatus of claim 3, wherein the texture of the contact surface includes raised longitudinal ribs.

5. The apparatus of claim 1, wherein the weighing element is adapted to measure the weight of the loose sand from between at least two times during the thermal erosion test to about continuously during the thermal erosion test, and to transmit the data to a data acquisition system.

6. The apparatus of claim 5, wherein the rotating heated element is adapted to extend through an opening in the specimen holder to press against the specimen at a pre-determined pressure.

7. The apparatus of claim 1, wherein the funnel is formed from a transparent material.

8. An apparatus for performing a thermal erosion test on a sand specimen, comprising:
    a heated element;
    a motor which is operably engaged with the heated element and rotates the heated element when the heated element is brought into contact with the sand specimen; and
    a member to collect loose sand abraded from the sand specimen by the rotation of the heated element.

9. The apparatus of claim 8, wherein the heated element has a shape which is generally conical or frustroconical.

10. The apparatus of claim 8, further comprising:
    a sand specimen supporting member, which supports the sand specimen above the heated element; and wherein the heated element is adapted to be raised to come into contact with the sand specimen during the thermal erosion test, and to apply a pre-determined pressure to the sand specimen during the thermal erosion test.

11. The apparatus of claim 8, wherein the heated element is rotated from about ¼ revolution to about 1 revolution while it is in contact with the sand specimen.

12. The apparatus of claim 11, wherein the heated element is adapted to be maintained at a temperature during the thermal erosion test which approximates a casting temperature of molten metal.

13. The apparatus of claim 8, wherein the member to collect loose sand abraded from the sand specimen by the rotation of the heated element is a funnel, and wherein the funnel is transparent.

14. A method of performing a friability test on a sand specimen, comprising the steps of:
    supporting the sand specimen, the sand specimen having a tapered hole therein, above a heated element;
    bringing the heated element and the sand specimen into contact, with the heated element adjacent the tapered hole of the sand specimen;
    rotating the heated element a pre-determined amount;
    collecting any loose sand abraded from the sand specimen; and
    weighing the loose sand.

15. The method of claim 14, further comprising the step of: observing the color of the loose sand.

16. The method of claim 14, wherein the step of weighing the loose sand comprises continuously weighing the loose sand during the friability test.

17. The method of claim 16, further comprising the step of:
    preparing a graphical representation of the weight of the loose sand with respect to elapsed time during the friability test.

18. The method of claim 14, wherein the step of rotating the heated element a pre-determined amount includes rotating the heated element from about ¼ rotation to about 1 rotation while the heated element is in contact with the sand specimen.

19. The method of claim 14, further comprising the steps of:
    heating the heated element to a temperature which approximates a casting temperature of molten metal; and
    pressing the sand specimen and the heated element together at a pre-determined pressure.

20. The method of claim 14, further comprising the steps of:

providing a tapered cylindrical guide and a hollow tube removably coupled to a generally disk-shaped base, with the tapered cylindrical guide extending generally perpendicularly from a center portion of the disk-shaped base, and with the hollow tube disposed radially outwardly from the tapered cylindrical guide, wherein a space is defined between the tapered cylindrical guide and the hollow tube;

compacting sand into the space between the tapered cylindrical guide and the hollow tube to form the sand specimen.

\* \* \* \* \*